United States Patent [19]
Beczak, Sr. et al.

[11] Patent Number: 5,599,287
[45] Date of Patent: Feb. 4, 1997

[54] HYPEREXTENSION ORTHOTIC APPARATUS USEFUL FOR TREATING PAIN ASSOCIATED WITH SPINAL DISORDERS

[75] Inventors: Terry A. Beczak, Sr., Wichita, Kans.; Thomas E. Szymke, Savannah, Ga.

[73] Assignee: Peach U.S., Inc., Wichita, Kans.

[21] Appl. No.: 539,018

[22] Filed: Oct. 3, 1995

[51] Int. Cl.$^6$ ........................ A61F 5/00
[52] U.S. Cl. ............... 602/19; 128/105.1; 128/95.1
[58] Field of Search ................ 602/5, 19; 2/44, 2/45; 128/876, 95.1, 96.1, 99.1, 106.1, 108.1, 102.1, 105.1

[56] References Cited

U.S. PATENT DOCUMENTS

| | | | |
|---|---|---|---|
| 2,760,486 | 8/1956 | Ward | 602/19 |
| 2,808,050 | 10/1957 | Ward | 602/19 |
| 3,220,407 | 11/1965 | Connelly | 602/19 |
| 3,282,264 | 1/1966 | Connelly | 602/19 |
| 3,420,230 | 1/1969 | Ballard | 602/19 X |
| 3,771,513 | 11/1973 | Valazquez | 602/19 |
| 3,945,376 | 3/1976 | Kuehnegger | 602/19 |
| 4,640,269 | 2/1987 | Goins | 602/19 |
| 4,926,257 | 12/1990 | Akin et al. | 602/19 |
| 5,342,289 | 8/1994 | Munny | 602/19 |
| 5,449,338 | 9/1995 | Trudell | 602/19 |

*Primary Examiner*—Linda C. Dvorak
*Attorney, Agent, or Firm*—Shook, Hardy & Bacon L.L.P.

[57] ABSTRACT

A hyperextension orthotic device is provided for treatment of back pain by causing uniform abdominal compression and hyperextension of the spinal column. The device includes a rigid brace having upper and lower pads for exerting pressure against the sternum and pubic area of an individual and a strap for causing a counterbalancing force to be applied to the back of the individual. The brace is coupled with a corset which causes abdominal compression to provide a stable base for the rigid brace.

8 Claims, 2 Drawing Sheets

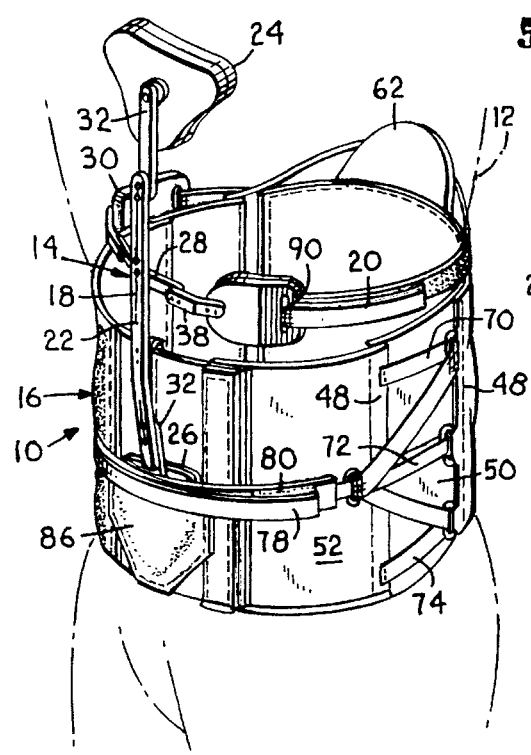
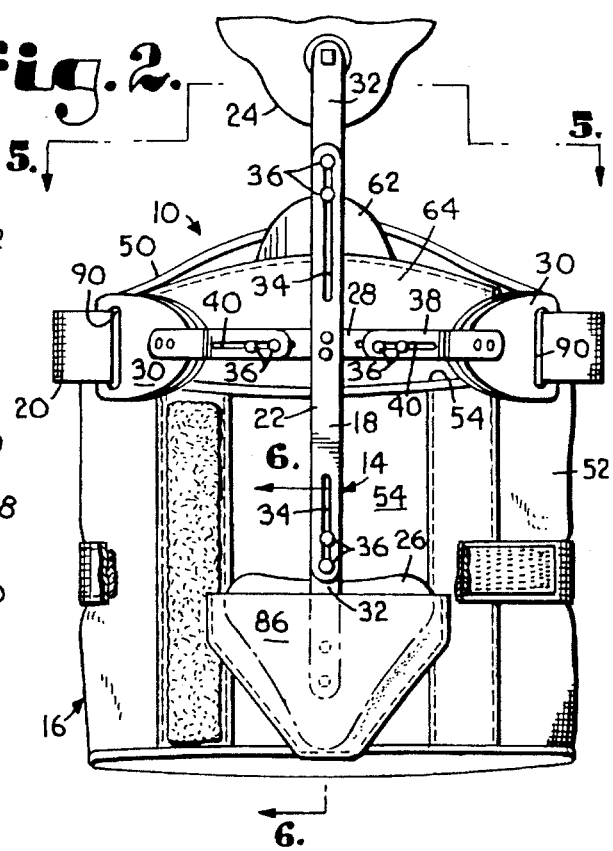
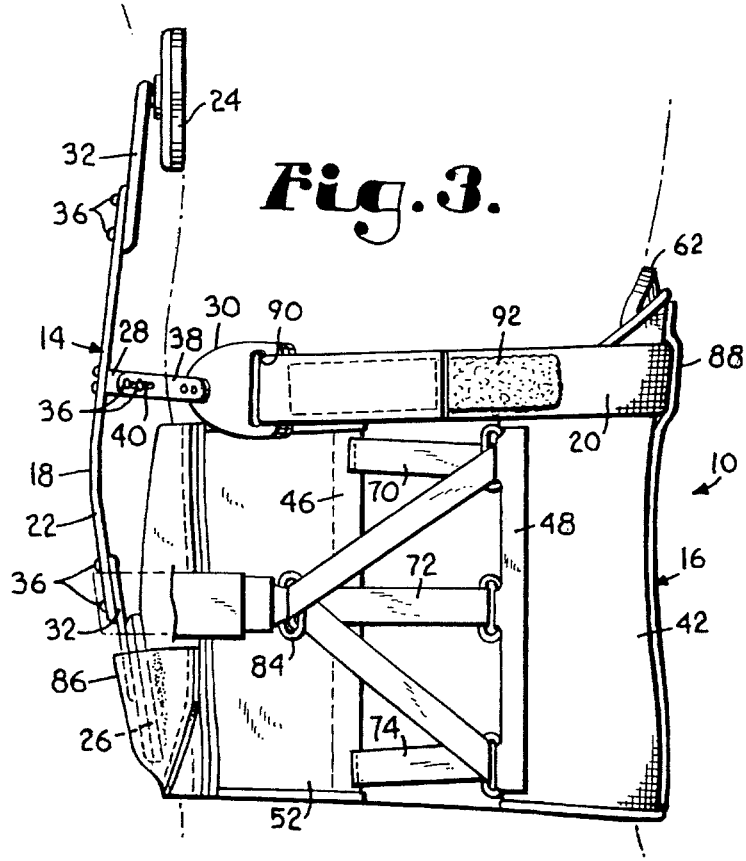

5,599,287

1

HYPEREXTENSION ORTHOTIC APPARATUS USEFUL FOR TREATING PAIN ASSOCIATED WITH SPINAL DISORDERS

BACKGROUND OF THE INVENTION

The invention is directed to braces or orthotic devices used in the treatment of spinal disorders and, more particularly, to hyperextension back braces used in the treatment of spinal disorders.

Hyperextension back braces are used to reposition the spine in a hyperextended position to alleviate the pain often associated with various types of spinal disorders. These braces may also serve to correct or prevent deformation of the spinal column, such as may result from the multiple compression fractures frequently experienced by women suffering from osteoporosis.

Conventional hyperextension back braces, such as disclosed in U.S. Pat. No. 4,173,973 to Hendricks, typically apply pressure at the pelvis and sternum of a patient. This pressure applied at the front of the thoracic region of the patient is then counterbalanced by pressure applied with straps and a posterior pad positioned at the desired location along the spine. By applying pressure in this three-point arrangement, the spinal column can be moved from a hyperflexed or slumped posture to a hyperextended position. When the spinal column is placed in the hyperextended position, the joint space between adjacent vertebra is increased, thereby relieving compressive pressure and associated pain along the spinal column.

A significant problem associated with conventional hyperextension back braces is the inability of these devices to sufficiently protect against vertical movement of the spinal column. During normal daily activities, an individual is likely to bend or otherwise move in a manner which causes further compressive loading along the length of the spinal column. This compressive loading can cause pinching of nerves between inter-vertebral discs with resulting momentary or prolonged pain. Conventional hyperextension back braces are designed to maintain the spine in a hyperextended position but are not well suited to reduce these compressive loading forces.

It has also long been recognized that certain types of lower back pain in humans can be treated by wearing corset type devices. These devices are applied around the torso of the individual and are tightened to cause an increase in the intra-abdominal pressure in the wearer. The increased intra-abdominal pressure in turn functions to reduce the compression force on the individual's spine by creating a semi-rigid hydra-pneumatic cylinder surrounding the spinal column. The load normally carried by the spine is distributed across this cylinder and the pressure on the lumbar inter-vertebral discs is correspondingly reduced. In many cases, the reduction in pressure also serves to provide dramatic relief in the pain associated with the spinal disorder.

SUMMARY OF THE INVENTION

It is an object of this invention to provide a hyperextension orthotic device which can be applied about the torso of an individual to place the spinal column in a hyperextended posture in a more stable manner than can normally be achieved by conventional devices.

It is also an object of this invention to provide a hyperextension orthotic device which places the spinal column in a hyperextended posture and which resists vertical compressive loading along the length of the spinal column to reduce the incidence of pain which might otherwise be experienced by the individual.

It is another object of this invention to provide a hyperextension orthotic device which achieves sufficient abdominal compression to alleviate back pain associated with disorders of the lumbar portion of the spinal column and which also causes hyperextension of the thoracic vertebra to alleviate pain associated with the thoracic portion of the spinal column.

To achieve these and other related objects of the invention, an orthotic device is provided for treatment of disorders of the spinal column. The device comprises:

- a generally rigid brace adapted to overlie an anterior thoracic portion of the human body, said brace comprising a generally vertical arm having an upper pad and a lower pad positioned at opposite ends of the vertical arm, said upper pad being adapted to contact the sternum and the lower pad being adapted to contact the pubic area of the body, said brace further comprising a strap coupled with said vertical arm and being adjustable for placement about the body to cause the upper pad and lower pad to exert a compressive force respectively on the sternum and pubic area with a counterbalancing force being exerted on a back portion of the body to cause hyperextension of a portion of the spinal column; and
- a corset coupled with the brace and adapted for wrapping around a torso of the body, said corset comprising a back panel formed to overlie a lumbar region of the spinal column, a front panel joined with the back panel to overlie an abdominal portion of the body, and means coupled with the front and back panels for allowing the front and back panels to tightened about said torso to cause an increase in intra-abdominal pressure.

BRIEF DESCRIPTION OF THE DRAWINGS

In the accompanying drawings which form a part of the specification and are to be read in conjunction therewith and in which like reference numerals are used to indicate like parts in the various views:

FIG. 1 is a perspective view of a hyperextension orthotic device of the present invention applied to the thoracic region of an individual partially shown in phantom lines;

FIG. 2 is a front elevation view of the hyperextension orthotic device;

FIG. 3 is a side elevation view of the hyperextension orthotic device shown applied to the individual partially shown in phantom lines;

DETAILED DESCRIPTION OF THE PREFERRED EMBODIMENTS

Figure 4:
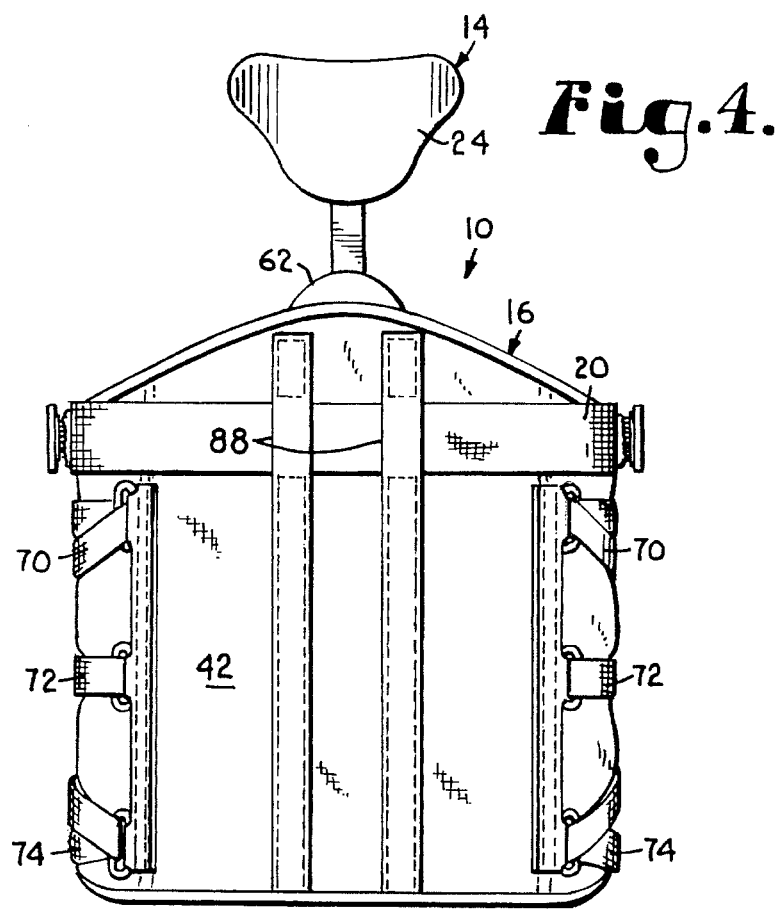
FIG. 4 is a back elevation view of the hyperextension orthotic device.
Figure 6:
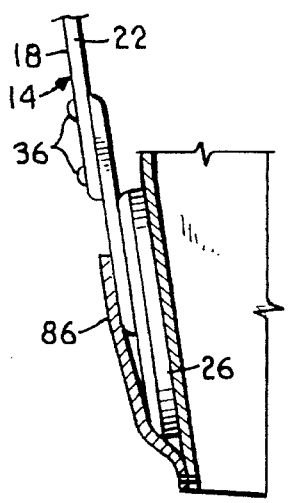
FIG. 6 is a fragmentary side elevation view taken in vertical section along line 6—6 of FIG. 2 showing a lower portion of the rigid hyperextension brace seated in a pocket of the corset portion of the orthotic device.
Figure 5:
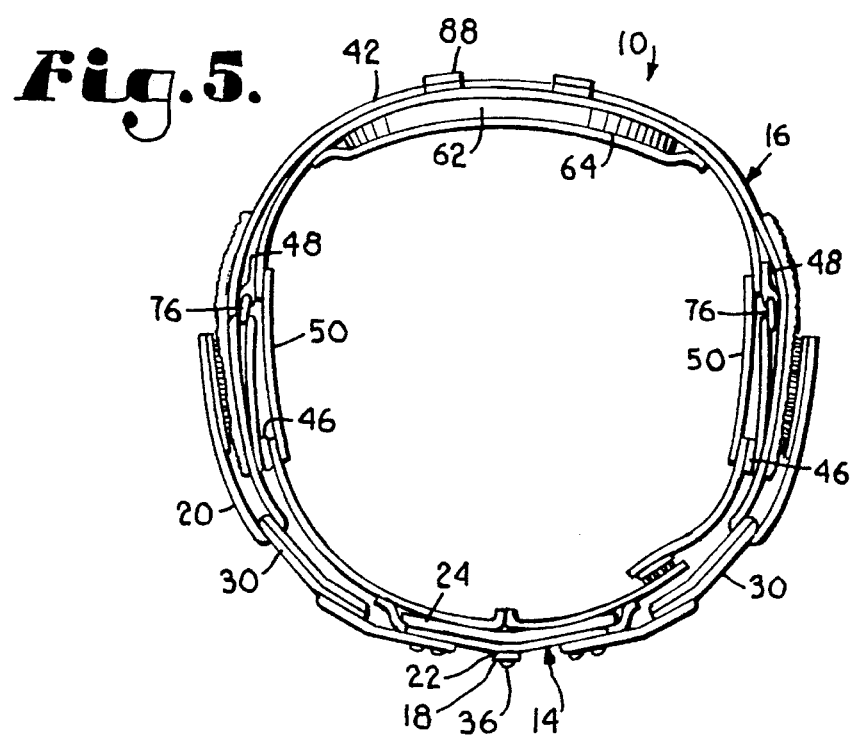
FIG. 5 is a top plan view of the device taken in horizontal section along line 5—5 of FIG. 2 in the direction of the arrows.

Referring now to the drawings in greater detail, a hyperextension orthotic device of the present invention which is used to place the spinal column in a hyperextended position and to resist hyperflexion is represented generally by the numeral 10. Device 10 is shown applied to a torso 12 of a human patient and comprises a rigid brace 14 and a corset 16.

Brace 14 includes a rigid cruciform structure 18 which is adapted to be placed on the anterior portion of the thoracic part of the human body and an adjustable strap 20 which is coupled with the cruciform structure 18 for tightening around the torso 12. The cruciform structure 18 comprises a vertical arm 22 having an upper sternum pad 24 and a lower pubic pad 26 adjustably mounted on opposite ends of the vertical arm 22. The sternum pad 24 is adapted to overlie and bear against the sternum of the patient while the pubic pad is similarly adapted to overlie and bear against the pubic region of the patient.

The cruciform structure 18 also includes a horizontal arm 28 which is fixed to the vertical arm 22 to form the cruciform shape for structure 18. Horizontal arm 28 carries two side pads 30 adjustably mounted at opposite ends of the horizontal arm. Side pads 30 are positioned to contact and bear against the left and right sides of the human torso 12 to reduce lateral shifting of the structure 18.

The sternum and pubic pads 24 and 26 are each fixed to a stub arm 32 which is aligned with the vertical arm 22. Means are provided for vertical adjustment of the stub arms 32 on the vertical arm 22 to allow placement of the sternum and pubic pads are the desired positions on the torso 12. The illustrated means for providing this vertical adjustment comprises an elongated closed-ended slot 34 formed in both ends of the vertical arm 22 and suitable fasteners 36 that extend through the slot 34 and are threaded into the stub arms 32 that carry the pads 24 and 26. The fasteners 36 may be loosened to permit vertical adjustment of the stub arms 32. Once the desired positioning is achieved, the fasteners 36 are tightened to prevent further movement of the stub arms along the slots 34.

The side pads 30 are similarly fixed to stub arms 38 that are aligned with and adjustably connected to the horizontal arm 28. Each stub arms 38 includes an closed-ended slot 40 and fasteners 36 extend through the slot 40 and are threaded to the horizontal arm 28 to permit lateral adjustment of the associated side pad 30.

The construction of the rigid brace 14 as described above is known in the art and is described in further detail in U.S. Pat. No. 4,173,973 to Hendricks which is incorporated herein by reference in its entirety. The present invention resides in the combination of the rigid brace 14 with the corset 16 in the manner described below.

The corset 16 is of a type which functions to reduce lower back pain in part by stabilizing the spinal column against undesired movement and maintaining the spine in the desired alignment. The corset 16 also serves to reduce lower back pain by increasing the intra-abdominal pressure to create a semi-rigid, hydra-pneumatic cylinder surrounding the spinal column. The cylinder shares the load normally carried by the spinal column and thereby reduces the vertical compression force exerted on the spine and the intervertebral disks which separate the spinal vertebrae.

Corset 16 comprises a back web or panel 42 which is formed to overlie the portion of the spinal column known as the lumbar region at the lower back of the human body. The back panel 42 may, and preferably does, have a vertical length to also overlie the lower thoracic portion of the spinal column at its upper end and the pelvis at its lower end. This vertical extension of the back panel 42 is advantageous because the pelvis and lower ribs serve to brace the lumbar, including against rotation.

The corset 16 also includes a front web or panel 44 which is formed to overlie the abdominal cavity or region at the front of the human body. The front panel 44 is coupled at its left and right lateral margins or edges 46 to corresponding left and right lateral edges 48 of the back panel 42 by side panels 50.

The front panel 44 of corset 16 is separated into left and right panels 52 and 54 which partially overlap and are joined together by a releasable fastener 56 along their vertical lengths to form a releasable seam. The seam allows the corset 16 to be opened to facilitate application and removal of the corset. The fastener 56 preferably comprises hook and loop type elements sold under the Velcro brand name but other types of fasteners could be used if desired. The fastener 56 should be capable of withstanding large shear stresses but should allow the left and right panels 52 and 54 to be readily joined and separated to allow the corset 16 to be easily applied and removed by the wearer. If desired, the seam formed by fastener 56 could be located elsewhere on the corset, such as in either side panel 50 or, less desirably, in back panel 42.

Various types of materials may be used in the construction of back panel 42, front panel 44 and side panels 50. Preferably, at least portions of the panels are formed of non-stretchable materials to allow a suitable compressive force to be exerted by the panels in the manner described below. Typically, the panels will be formed of textile fabrics such as cotton but synthetic fabrics as well as non-woven materials could be used instead. The panels 42, 44 and 50 can be formed from separate pieces of the same or different materials which are sewn or otherwise joined together along their lateral edges. Alternatively, a single piece of material can be used to form the panels. A plurality of stays 58 can also be formed in the panels to provide vertical support for the panels.

The corset 16 optionally includes elastic sections 60 which are formed of stretchable or elastic material to allow the corset to conform to the physical variations of the individual wearing the corset 16. The elastic sections 40 are preferably positioned only at the upper margin of the corset 16 so that generally continuous center and lower bands of non-stretchable material are presented by the panels 42, 44 and 50. Although the size, shape and placement of the elastic sections 40 can be varied as desired, it is generally preferred that the elastic sections be placed at the upper margin of the front panel 44.

A rigid back board 62 is also included in the corset 16 to provide a broad rigid surface to support and stabilize the spinal column. The back board 62 is removably positioned within a pocket 64 formed on a forward surface of the back panel 42. The back board 62 is preferably formed of a thermoplastic material to permit the back board to be specifically conformed to the contours of the lower back of the individual wearing the corset 16. An example of a suitable material is a low temperature thermoplastic sold by Johnson & Johnson under the trademark Orthoplast. If desired for comfort purposes, a forward face of the back board 62 can be covered with a pad such as formed of a polyethylene foam.

Leveraged circumferential pressure, with resulting increased intra-abdominal pressure, is exerted by the corset 16 on the trunk or torso of the individual wearer through the use of suitable strap means 66 which join together the front and back panels 44 and 42. The strap means 66 comprises a left strap 67 and a right strap 68 which are operable to draw the lateral edges of the back panel 42 toward the lateral edges of the front panel 44. The free ends of the straps 67 and 68 may be fastened at the front of the corset 16 to allow the wearer of the corset to gain a mechanical advantage when tensioning the straps to cause exertion of the circumferential pressure on the wearer's torso. Notably, the straps 67 and 68 utilize a pulley-type system which leverages the applied mechanical force so that increased intra-abdominal compression can be obtained.

Both of the left and right straps 67 and 68 are formed of generally non-stretchable material and comprise vertically spaced apart upper, intermediate or center and lower belts 70, 72 and 74. Each belt 70, 72 and 74 is secured at one end to a respective lateral edge of the front panel 44 with the upper belt 70 being located at the upper vertical margin, the lower belt 64 being located at the lower vertical margin and the center belt 72 being located at a vertically intermediate position on the corset 16. The belts then extend rearwardly from their respective areas of attachment at the lateral edges of the front panel 44 and are coupled with the corresponding lateral edges of the back panel 42 in a pulley-type arrangement. The belts are coupled with the lateral edges of the back panel 42 by individual fastening elements 76 which serve as pulleys to permit longitudinal extension of the belts through the fastening elements. Various types of fastening elements 76 can be utilized for this purpose but elongated metal loops or rings are generally preferred because of their strength and rigidity. In addition, the metal rings have a low coefficient of friction which minimizes the wear on the belts 70, 72 and 74 as they are moved back and forth through the rings. The low coefficient of friction also allows the compressive force exerted by the left and right straps 67 and 68 to be readily released without the time-consuming manipulation of laces or other conventional fastening elements.

In use, the belts 70, 72 and 74 are doubled back upon themselves after passing through their respective fastening elements 76 and extend forwardly to the front of the corset 16 and are coupled together at a vertically intermediate position of the corset. A wider tensioning belt 78 is secured to and is in longitudinal alignment with the center belt 72 of each of the left and right straps 66 and 68. It is to be understood that each tensioning belt 78 may simply be part of or an extension of the associated center belt 72. The tensioning belts 78 are of a sufficient length to at least partially overlap at the front of the corset 16. The tensioning belts 78 include a suitable fastener 80 such as formed by hook and loop elements which allow the tensioning belts to be joined together at the front of the corset. Preferably, one of the tensioning belts 78 can also be joined to the front panel 44 by another fastener 82. Alternatively, the tensioning belts 78 can simply be fastened together without being joined to the front panel 44 or both tensioning belts 78 can be independently secured to the front panel 44 by fasteners.

The positioning of the tensioning belts 78 at the front of the corset 16 is particularly advantageous because they may be readily grasped and manipulated by most individuals using a natural hand and arm motion. Even weak and infirm individuals are generally capable of exerting sufficient force on the tension belts 78 to cause the necessary constriction of the corset 16 about the individual's torso.

The tensioning belts 78 are also secured to the upper and lower belts 70 and 74 in a manner so that a longitudinal force exerted on each tensioning belt is leveraged and is also uniformly conveyed to the upper and lower belts as well as the center belt 72. The connection of the upper and lower belts to the tensioning belt is notable in this regard because it permits automatic adjustments in the lengths of the upper and lower belts, with an increase in the length of one of the belts causing a corresponding decrease in the length of the other belt. This allows the upper and lower belts 70 and 74 to automatically adjust to accommodate the expected variations in the circumferential dimensions about the wearer's lower ribs, waist and hips. The adjustment of the belt length in this manner also allows each of the upper, center and lower belts 70, 72 and 74 to exert a uniform circumferential pressure on the torso of the wearer at vertically spaced apart locations.

The automatic adjustment of the length of the upper and lower belts 70 and 74 is achieved by forming the upper and lower belts from a single length of material or otherwise joining their free ends together to form a single belt which is extensible through a fastening element 84 joined to an end of the associated tensioning belt 78, preferably near the connection of the center belt 72 with the tensioning belt 78. The fastening element 84 is preferably a metal ring of the type previously described which functions as a pulley to permit ready movement of the single belt through the ring. The fastening element 84 thus allows the upper belt 70 and lower belt 74 to increase and decrease in length as is necessary to accommodate the particular physique of the wearer, with an increase or decrease in one belt causing a corresponding decrease or increase in the other belt. This automatic adjustment in the respective lengths of the upper and lower belts allows a circumferential tensioning force which is uniform along the vertical length of the corset 16 to be applied to the torso 12 of the wearer. It can be appreciated that the uniform tensioning force is desirable not only from a comfort standpoint but also to ensure that the compression force on the spine is uniformly reduced.

Notably, the series of pulley-type fastening elements 84 operate to leverage the mechanical force applied to the left and right straps 67 and 68 by the wearer of the corset 16. This ability to leverage the applied mechanical force allows the desired intra-abdominal compression to be achieved by even weak and otherwise infirm individuals. As a result, such individuals are able to be more self-sufficient than would be possible if conventional corsets were utilized.

In accordance with the present invention, the corset 16 is used in association with the rigid brace 14 to provide a stable base for the brace 14 with reduced opportunity for hyperflexion of the spinal column. The corset 16 is associated with the brace 14 in part by seating the lower pubic pad 26 of the brace 14 within a pocket 86 provided on the exterior of the front panel 44. The pocket 86 is open at the top and closed at the bottom to allow the pubic pad 26 to be downwardly inserted into the open top of the pocket 86. Further downward movement of the brace 14 in relation to the corset 16 is thus prevented once the pubic pad 26 is seated within the pocket 86.

The brace 14 is also coupled with the corset 16 by the circumferential strap 20 that extends through a pair of spaced apart loops 88 formed in the back panel 42 and is joined to the left and right side pads 30. The side pads 30 include suitable reinforced openings 90 through which the ends of the strap 20 are inserted. The strap ends are then doubled back upon themselves and are secured using suitable hook and loop fasteners 92. The strap 20 thus can be readily tightened to cause the desired amount of force to be applied by the upper sternum pad 24 against the individual's sternum. This force on the sternum is counterbalanced by the force exerted by the back board 62 on a broad region of the individual's back.

The hyperextension orthotic device is applied to the torso 12 of the individual experiencing back pain by wrapping the corset 16 about the torso and joining the hook and loop elements which form the fastener 56 at the left and right front panels 52 and 54. The individual can then achieve the desired abdominal compression by simply grasping and pulling the tensioning belt 78 of the left strap 67 across the front of his or her body. Exerting this longitudinally directed force on the tensioning belt 78 causes the associated upper, center and lower belts 68, 70 and 72 to pull the lateral edge of the corset front panel 44 toward the lateral edge of the corset back panel 42. At the same time, the respective lengths of the upper and lower belts 68 and 72 automatically adjust as necessary to permit the corset 16 to conform to the underlying portions of the wearer's body. This pulling action of the belts causes a circumferential force to be exerted on the torso with resulting abdominal compression. Once the desired compression is achieved, the left strap 67 can be secured by joining the associated tensioning belt 78 to the front panel 44 by the use of fastener 82.

After or while the left strap 67 is being tensioned and secured, the right strap 68 can be grasped and likewise tensioned, causing further abdominal compression. The right strap 68 is then secured by overlapping its tensioning belt 78 with the tensioning belt associated with the left strap 67 and joining together the hook and loop elements which form fastener 80. It can be readily appreciated that the desired abdominal compression can be easily obtained with the use of the left and right straps 67 and 68 in the manner described.

It can be seen that the secured left and right straps 67 and 68 overlap the lower portion of the rigid brace 14 at a location just above the pubic pad 26. The compression force exerted by the straps thus advantageously acts to retain the pubic pad 26 in the desired position and causes the pubic pad 26 to bear against the pubic region of the individual with a force corresponding to the compression force. If desired, the straps 67 and 68 can be placed posteriorly of the rigid brace 14 so that the compressive force is not exerted on the pubic pad 26.

The rigid brace 14 is then further secured by tensioning the strap 20 which is connected to the side pads 30 of the brace. Tensioning of strap 20 causes opposing forces to be exerted by the sternum pad 24 on the sternum and by the back board 62 on the back of the individual. Because the back board 62 covers a broad area of the individual's back, the force exerted by the tensioned strap 20 is distributed over a larger area and is less likely to cause patient discomfort as may result from the smaller pads used with conventional devices.

It can thus be seen that the hyperextension orthotic device 10 operates to place the thoracic portion of the spinal column in a hyperextended position to relieve pain associated with various types of spinal disorders. The device 10 also serves to reduce lower back pain by increasing the intra-abdominal pressure to create a semi-rigid, hydra-pneumatic cylinder surrounding the spinal column. This cylinder shares the load normally carried by the spinal column and reduces the vertical compression force exerted on the spine and the intervertebral disks. Importantly, this cylinder also provides a more stable base for maintaining the thoracic vertebrae in the hyperextended position and resisting hyperflexion of the spine. In addition, the stability provided by the corset 16 reduces the up and down movement of the rigid brace that is normally experienced as the individual engages in daily activities. The device 10 thus affords greater stability to the spinal column and can readily relieve the pain associated with many types of spinal disorders.

From the foregoing, it will be seen that this invention is one well adapted to attain all the ends and objects herein- above set forth together with other advantages which are inherent to the structure described.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. An orthotic device for treatment of disorders of the spinal column, said device comprising:
   a generally rigid brace adapted to overlie an anterior thoracic portion of the human body, said brace comprising a generally vertical arm having an upper pad and a lower pad positioned at opposite ends of the vertical arm, said upper pad being adapted to contact the sternum and the lower pad being adapted to contact the pubic area of the body, said brace further comprising a strap coupled with said vertical arm and being adjustable for placement about the body to cause the upper pad and lower pad to exert a compressive force respectively on the sternum and pubic area with a counterbalancing force being exerted on a back portion of the body to cause hyperextension of a portion of the spinal column; and
   a corset coupled with the brace and adapted for wrapping around a torso of the body, said corset comprising a back panel formed to overlie a lumbar region of the spinal column, a front panel joined with the back panel to overlie an abdominal portion of the body, and means coupled with the front and back panels for allowing the front and back panels to be tightened about said the torso to cause an increase in intra-abdominal pressure.

2. The device as set forth in claim 1, including means for releasably coupling said lower pad of the brace with the front panel of the corset.

3. The device as set forth in claim 1, wherein said strap is coupled with the back panel of the corset.

4. The device as set forth in claim 1, including a horizontal arm joined to the vertical arm and having side pads positioned at opposite ends of the horizontal arm, said strap being coupled with said side pads to cause the side pads to exert a compressive force against the torso.

5. The device as set forth in claim 1, wherein said means coupling said back panel with said front panel comprises a right strap coupling right lateral portions of said back and front panels and a left strap coupling left lateral portions of said back and front panels, each of said right and left straps comprising vertically spaced belts secured at one end to the respective lateral portion of the front panel and extending rearwardly through retention members fixed at vertically spaced positions on the respective lateral portion of the back panel and then forwardly for joinder at the front panel, said belts being longitudinally extensible through said retention members to permit adjustment of a distance of separation between the respective right lateral portions of the back and front panels and the left lateral portions of the back and front panels.

6. The device as set forth in claim 5, wherein said belts comprise an upper belt secured at said one end near an upper margin of the front panel, a lower belt secured at said one end near a lower margin of the front panel and an intermediate belt secured at said one end at a vertically intermediate position on the front panel.

7. The device as set forth in claim 6, wherein said upper and lower belts in at least one of the left and right straps are coupled such that an increase or decrease in length of the upper belt causes a corresponding decrease or increase in the lower belt.

8. The device as set forth in claim 5, wherein said left and right straps overlie the lower pad on the brace when fastened together.

* * * * *